United States Patent
von Mueller et al.

(10) Patent No.: US 9,355,353 B2
(45) Date of Patent: May 31, 2016

(54) METHOD AND SYSTEM FOR SUPPORTING THE DIAGNOSIS OF AN OBJECT HAVING AT LEAST ONE DISTURBANCE

(75) Inventors: Albrecht von Mueller, Icking (DE); Martin Hirsch, Marburg (DE)

(73) Assignee: MEDPAD GMBH, Munich (DE)

( * ) Notice: Subject to any disclaimer, the term of this patent is extended or adjusted under 35 U.S.C. 154(b) by 228 days.

(21) Appl. No.: 14/111,275

(22) PCT Filed: Apr. 10, 2012

(86) PCT No.: PCT/EP2012/001553
§ 371 (c)(1),
(2), (4) Date: Dec. 23, 2013

(87) PCT Pub. No.: WO2012/139749
PCT Pub. Date: Oct. 18, 2012

(65) Prior Publication Data
US 2014/0122380 A1  May 1, 2014

(30) Foreign Application Priority Data
Apr. 11, 2011 (DE) .......................... 10 2011 016 691

(51) Int. Cl.
*G06N 5/02* (2006.01)
*G06F 19/00* (2011.01)
*G06T 11/20* (2006.01)
*G06N 99/00* (2010.01)
*G06F 17/30* (2006.01)

(52) U.S. Cl.
CPC ............ *G06N 5/02* (2013.01); *G06F 17/30994* (2013.01); *G06F 19/345* (2013.01); *G06F 19/3443* (2013.01); *G06N 99/005* (2013.01); *G06T 11/206* (2013.01)

(58) Field of Classification Search
CPC combination set(s) only.
See application file for complete search history.

(56) References Cited

U.S. PATENT DOCUMENTS

| | | | |
|---|---|---|---|
| 2002/0013720 A1 | 1/2002 | Ozono et al. | |
| 2006/0061589 A1 | 3/2006 | Suyama et al. | |
| 2008/0215543 A1 | 9/2008 | Huang et al. | |
| 2009/0094053 A1 | 4/2009 | Jung et al. | |
| 2012/0070044 A1* | 3/2012 | Avinash ............... | G06K 9/3233 382/128 |

OTHER PUBLICATIONS

Internet Archive WaybackMachine, "Grapher" from Mar. 29, 2009, from website http://web.archive.org/web/20090328122320/http://www.goldensoftware.com/products/grapher/grapher-graphtypes.shtml.

* cited by examiner

*Primary Examiner* — Alan Chen
(74) *Attorney, Agent, or Firm* — Greer, Burns & Crain, Ltd.

(57) ABSTRACT

A method and apparatus are provided for aiding diagnosis of an object showing a disorder and for selecting a finding characterizing the state of the object. Each finding is described as a visual pathology by a severity, a symptom constellation of multiple symptoms and by a graphic representation of the symptom constellation. A dialog-based, visual modelling of the state of the object is provided wherein the state of the object is modelled by a current symptom constellation represented by a symbol. The resulting, current object image is immediately graphically output on the display device. Following each case of modification a comparator immediately compares the current symptom constellation against the symptom constellations of stored findings and updates the list of findings of potentially applicable findings. A list of suggestions for examining further symptoms is output, sorted by their differentiation so as to interactively facilitate diagnosis.

15 Claims, 3 Drawing Sheets

METHOD AND SYSTEM FOR SUPPORTING THE DIAGNOSIS OF AN OBJECT HAVING AT LEAST ONE DISTURBANCE

BACKGROUND

The present invention relates to a method and a system for aiding diagnosis of an object showing at least one disorder and for selecting findings that characterise at least part of the state of the object wherein use is made of a number of findings stored in at least one data base.

The invention in particular relates e.g. a method for aiding medical doctors in diagnosing diseases. The doctor will not be relieved from deciding on a diagnosis but after entering symptoms a selection of diagnoses is displayed that best compare to the symptoms of the patient and their assessment by the attending physician.

The invention likewise relates to a method and a system in which an expert is aided in analysing a complex object showing at least one disorder.

Various methods and systems for aiding in selecting findings have become known in the prior art. A doctor may for example enter all the symptoms of a patient into a data base and he will receive a list of diseases having precisely these symptoms.

It is likewise possible for example when diagnosing disorders in complex technical systems, to enter all the irregular measurement values and operating conditions whereupon a selection of the possible sources is provided.

All of these methods and systems work reliably per se. There is, however, the drawback for example when diagnosing diseases that a patient may suffer from an atypical form of a disease not showing what is actually a typical characteristic (symptom) and which had not been described previously. This may result in a faulty diagnosis because the doctor will possibly not consider this specific disease. With the known methods this disease will not be indicated due to the absence of what is actually a typical symptom. Another problem in diagnosis may arise if the patient suffers from two diseases whose symptoms overlap. Then a data base query including all the symptoms will not yield a result. Another problem of existing methods consists in that the "gut feeling" of a doctor is not taken into account for the significance of a symptom in view of the course of the disease. Thus e.g. vomiting in the context of vertigo is less significant (since it tends to be an accompanying symptom) than in the context of bloody stools.

Also when diagnosing for example a defective motor vehicle, not all the marks of the current malfunction will be essential. The expert in charge of repairs will know due to his experience that a dent in the fender is not significant for a worn out seat cover. When the running engine knocks the source may be a defect in engine control. Or else the source might be nonconforming fuel in the tank.

In the case of complex technical products there may be multiple defects unrelated to one another which impedes diagnosis.

SUMMARY

It is therefore the object of the invention to provide a method and a system for aiding in the selection of a reference state of disorder for the state of an object to allow the user a neat, reliable selection function.

The method according to the invention serves for aiding diagnosis of an object showing at least one disorder and for selecting findings that characterise at least part of the state of the object wherein a number of findings is stored in at least one data base which may be referred to for aiding. Each of the findings stored is described by the severity or seriousness of the finding and by a symptom constellation of a number of symptoms. In this respect the severity of findings is not a characteristic or symptom but indicates e.g. the seriousness of the disease or the disorder. A graphic representation of the symptom constellation defines a visual pathology of the findings. Each symptom shows at least one symptom type and at least one expression. Each symptom in each pathology is represented by a symbol the coordinates of which are determined in a first dimension by the type of the symptom and in a second dimension by the expression of the symptom.

The method provides for a dialog-based or interactive, visual modelling of the state of the object. What is the current state of the object is described by a current symptom constellation which may comprise one symptom or in particular multiple symptoms. Each symptom shows at least one symptom type and at least one expression. The current symptom constellation defines an object image wherein each symptom in the object image is represented by a symbol the coordinates of which are determined in a first dimension by the symptom type of the symptom and in a second dimension by the expression of the symptom. This means that the object picture and the pathology are basically structured by the same principles so as to result in visually comparable pictures.

To aid diagnosis, at least one in particular mobile computer, at least one comparator, at least one input device and at least one display device are provided. The comparator may be part of the computer or else be configured separately.

The following process steps are carried out in particular for starting:
  A current symptom constellation is derived from a pre-defined symptom constellation,
  a current list of findings is derived from a pre-defined list of findings containing stored findings, and
  a current list of suggested symptoms is derived from a pre-defined list of suggested symptoms.

The following process steps are automatically repeated preferably in a loop in this or another suitable sequence until a finding is determined or entered manually, or until a pathology and thus the pertaining finding is selected or until the process is abandoned:
a) By way of the input device that is in particular interactive, mobile, and preferably gesture-controlled, at least one symptom of the current symptom constellation is modified, preferably by way of gesture control, for modelling the state of the object. The symptom constellation thus modified is stored as the current symptom constellation. The current symptom constellation is automatically, graphically output on the display device as the current object image. In practice this means that the current symptom constellation is interactively, visually generated by the user as being the current object image.
b) The comparator immediately and automatically compares, following each case of symptom modification, the current symptom constellation against the stored symptom constellations of the findings of the current list of findings and represents the results of the comparison immediately on the display device and thus in the field of vision of the user. This immediateness of the presentation of the results of the comparison is an essential component of the system since only such immediateness establishes a conversational relationship between the user and the system which is required for the system to output suggestions and e.g. introduce new, situation-relating information into the current diagnostic thought processes of the user. The immediateness is also of particular significance since it alone allows to playfully obtain a type of IF-THEN simulations. The expert may by way of testing "simply" modify a symptom by means of a gesture for checking what reference objects will then be displayed. This is a significant advantage of the inventive method since it allows and furthers such a playful, experimental, intuitive procedure.

c) The comparator immediately and automatically compares, following each case of symptom modification, the current symptom constellation against the stored symptom constellations of the findings of the current list of findings and directly deletes from the current list of findings those findings showing a congruence with the current symptom constellation that remains beneath a predetermined, first value. Comparison may occur e.g. graphically or numerically.

d) The comparator automatically compares, following each case of symptom modification, the current symptom constellation against the symptom constellations of the findings stored in the data base and immediately adds to the current list of findings those stored findings showing a congruence of the respective symptom constellation with the current symptom constellation that lies above a predetermined, second value. Comparison may also occur e.g. graphically or numerically.

e) The current list of findings is immediately and automatically sorted by the computer following each case of symptom modification, which sorting takes into account the similarity of the current symptom constellation with the respective symptom constellation of the stored findings and the severity of the stored findings.

f) At least one finding of the current list of findings is used to plot onto the display device the pertaining symptom constellation as the pathology, if the current list of findings at all includes relevant findings. In particular are the respective symptom constellations of two, three or more of the most relevant or most similar findings of the current list of findings plotted as the pathology.

g) The comparator automatically compares, following each case of symptom modification, the current list of suggested symptoms against the symptoms of the findings of the current list of findings, and re-sorts the current list of suggested symptoms. The current list of suggestions is stored and output immediately.

The method according to the invention has many advantages. By way of the visually interactive and in particular mobile entry of symptoms characterizing the state of the object the expert is aided in attaining findings on site. What is relevant is presently to provide the respective expert with suggestions for and aid in diagnosis immediately on location, e.g. at the sickbed. However, the actual diagnosis will always be left to the expert.

In the case of specific disorders for example in complex technical systems the expert knows when hearing the noise e.g. of a motor that something is wrong without directly identifying the source of the problem. Now the invention is not primarily concerned with searching for findings showing similar symptoms but with providing the expert, based on a systematic, visually assisted comparison, immediately and on site, with suggestions of further symptoms and probably examinations which finally result in determining a finding and thus in knowledge of the causal problem and feasible actions to remedy the disorder. What is concerned is thus in particular to entice the idea from the expert but not to relieve him of making a diagnosis. The method according to the invention utilises the creativity of the expert and serves as a tool for aiding diagnosis but does not actually make a diagnosis.

The invention allows easy visualising of various stored findings and comparison against the state of the object as it had been entered so far. By way of visual comparison the expert obtains ideas and suggestions about what symptoms allow high differentiation so as to make an efficient analysis.

In the case of sharply defined selection processes as in the prior art, a Boolean logic control of symptoms or the traversing of a decision tree tends to complicate the attaining of a correct result. The present invention does not specify any decision tree and/or firm sequence schedule but due to a background computing process supplies the expert using the system with similar findings, displaying relevant symptoms which provide ideas and suggestions for finding the solution.

A considerable advantage of the method according to the invention consists in the interactive, graphic processing of symptom constellations so as to allow easy and quick visual comparison to one another and modification preferably using few gestures.

It is possible for the pre-defined symptom constellation to be a "blank" symptom constellation to which thus a blank object image is first assigned. Specifying such a pre-defined symptom constellation for the current symptom constellation as the process begins has the diagnosis start at "zero". Or else a previously stored symptom constellation that was for example previously stored serves as the pre-defined symptom constellation.

The method in particular also provides for a storing means to allow to resume and continue the process at any time.

The pre-defined list of findings may again be a "blank" or previously filled list of findings used as the basis when starting the process.

The pre-defined list of suggested symptoms may comprise all of the symptoms and it may first be sorted in some way.

Each symptom constellation is defined by a number of symptoms each exhibiting a symptom type and a respective expression. A significant item of the invention is the fact that each symptom carries and indicates information about its significance in respect of the disorder's source. For example, given a specific clinical picture there may be a symptom that an experienced physician will consider to be not particularly relevant or else specifically particularly characteristic (so-called guiding symptoms). Accordingly the significance of a symptom may express itself, or be assessed, to a lesser or higher degree. Due to this condition the method according to the invention may for example provide for relevant symptoms to be arranged in a circle near the centre and less relevant symptoms, remote from the centre to thus benefit the intuitive interpretation by the expert.

A considerable advantage of the method according to the invention also consists in the fact that it is cognitively robust versus symptom fluctuations. The graphic illustration of the symptom constellations and comparison of the symptom constellation against the stored symptom constellations allow the user an easy and quick graphic, visual overview of which of the stored symptom constellations are suitable to be selected in the case concerned, and how they differ. In this way the selection of possible findings can be very quickly much restricted such that only relevant objects to be selected remain with which the user can deal more intensely.

Preferably at least one view area and at least one selection area are provided. The view area and the selection area may be arranged on one shared display device or on separate display devices. Outputting the object image preferably occurs in the view area and outputting the at least one pathology preferably occurs in the selection area.

The input device is provided for modifying in each method step at least one symptom of the state of the object, i.e. in particular for entering, deleting, or changing. Following modification the current symptom constellation is stored.

Preferably, modification or entry of at least one symptom of the current symptom constellation occurs by a graphically interactive input. Input may for example occur by way of swipe gestures.

Due to the fact that at least one stored finding or its symptom constellation is graphically displayed in the selection area, a simple comparison of this graphic layout against the graphic layout in the view area allows what to the human brain is a very efficient, visual comparison that attains high reliability when selecting one or more stored findings. It is in particular not required to compare each single symptom with one another but a simple graphic comparison of layouts allows a rather reliable assess which of the stored layouts shows the best congruence with the current symptom constellation to be determined. To this end the stored findings are graphically edited in the selection area in the same way as are the symptoms of the state of the object to be determined in the view area.

In particular is it not required to compare a textual description in tabular form or the like of each single symptom against the description texts of the stored objects.

When in diagnosing a disease each of the symptoms of the patient is represented by a symbol in or on the view area, then the total number of symbols of the patient will on the whole show a graphic layout or a symptom constellation characteristic of the condition of the patient. Each symbol is characterised by the type or class of the symptom in particular in respect of a first coordinate while the second dimension or the second coordinate for arranging the pertaining symbol defines the significance of the related symptom. It is a substantial component of the method according to the invention that presently it is not an objectively metric aspect (such as the temperature value measured) that determines the position but a subjectively assessing aspect. In this way the method includes "the gut feeling" of the expert in the process of comparison and this is exactly what the method according to the invention is about.

For example if the patient has a headache, then the type "headache" may be selected for the symptom type. The term "significance" or "relevance" is understood to mean in the sense of this application whether the symptom is of central importance for the course of the disease or whether it is rather an accompanying symptom. "Intensity" or "expression" is preferably understood to mean the degree of expression of the respective symptom. (How strong is the headache on a numeric pain scale?)

With other objects e.g. products such as motor vehicles and the like the symptom type may for example describe the knocking of a motor while the expression may, depending on the rest of the constellation, be significant (=e.g. strong) or unimportant. When assessing threadbare seat covers the knocking of the motor is of secondary importance while when assessing engine problems such a symptom will be given a clearly higher mark.

In all the configurations it is particularly preferred to chose a coordinate system where the symptom type is plotted over the angle while the significance (relevance) is a function of the radius or of the distance from a centre point or an axis, and the intensity or the degree of expression is expressed by the size of the symbol. It is possible that with increasing importance the radius, i.e. the second coordinate, decreases, while the radius increases with decreasing significance and thus decreasing importance. For example the view area and/or the selection area may be defined by a surface wherein different symptoms, i.e. different symptom types, are plotted over the angle and a particularly high importance is mapped near the centre. By way of associating the symptom type with the angle it is ensured that for example headaches, limb pains, or abdominal pain, are arranged in different angular positions while the angular position of a specific symptom always remains the same. Thus where the diagnosis of a disease is concerned, headache is as a rule plotted in the same angular position so as to substantially enhance recognition. The importance of the respective symptom in the pathological development is described by its proximity to the centre such that symbols are placed close to the centre which for example in the opinion and assessment of the attending physician show a high relevance of the pertaining symptom to the current diagnosis. The intensity or the degree of expression of the symptom is defined or encoded by the size of the symbol.

Or else it is possible to draw up an X-Y diagram where the X coordinate represents the symptom type and the relevance is represented on the Y coordinate. A particularly high relevance may correspond to a high Y value or a low Y value. In this kind of representation a graphic layout of multiple symptoms is again characteristic of specific findings. This allows via simple comparison of layouts a concentration on very few stored findings.

When employing the method according to the invention in aiding medical diagnoses the basic goal is not to replace the doctor and to obtain a simple diagnostic system but to aid the experienced physician in making a diagnosis by way of recalling clinical pictures and symptoms which fit into the current symptom constellation but which are rather rare in practice and which the doctor may thus readily forget or overlook. Thus for example the symptom "vertigo" may be a factor in a plurality of different diseases and thus diagnoses. The same applies to the symptom "abdominal pain" e.g. in children. Even an experienced medical specialist may have difficulties finding a suitable diagnosis with these symptoms since the clinical pictures include different quantities of symptoms in different degrees of expression. In particular since these symptoms may occur in so-called orphan diseases which a physician—even a medical specialist—may rarely or never encounter in his professional practice, it is conceivably hard to make a correct diagnosis.

The invention presently allows by way of comparing layouts, a comparison of different symptom constellations such that in the case of diagnosing diseases the physician will also be shown symptom constellations that are rare but may still show high congruence with the current symptom constellation.

In this example it is again important for the method according to the invention to capture and map what the attending physician may subjectively perceive as a significant symptom.

The same applies to complex technical installations where isolated disorders may originate from a great variety of sources. The findings may be severe or only of secondary importance. Unusual noises in a turbine in a superpower station may e.g. be indicative of defective bearings. In this case it should also be captured what findings in the view of the expert have what significance for the occurrence causing disorders. A method according to the invention allows to quickly find out in these installations whether a severe problem is in fact present or whether there is only some damage to be remedied easily involving little potential of damage.

In a preferred embodiment of the invention the selection area displays at least two different, stored symptom constellations. Each of the two different symptom constellations is plotted in a separate window or display fields or areas such that each of the symptom constellations is plotted independently by itself. Three or more different, stored symptom constellations are in particular displayed for selection such that the user may make a selection by means of the layouts of each of the symptom constellations.

In the sense of this invention the state of an object may correspond to a disease or a diagnosis which is a function of different symptoms and thus different characteristics.

During or else at least immediately following the input or modification of each of the symptoms the displayed selection of stored objects is changed in the selection area. It is for example possible for single stored symptom constellations to become more probable if a large number of symptoms is identical. Then the respective pertaining findings or symptom constellations are preferably displayed.

In all the configurations it is preferred for at least one symptom to comprise the further property of intensity. For example if the invention is employed in diagnosing diseases then the symptom "headache" may in the opinion of the attending physician be highly significant for the disease present. It is, however, possible that the "headache" shows high or else weak intensity. Consequently the intensity of a symptom suggests itself as another parameter. A weak headache may be highly concise for specific diseases in combination with further symptoms.

Preferably the list of findings will thus be influenced by the sequence of the displayed findings in the selection area or of the display of the stored findings by the degree of differentiation of stored findings from the entered symptom constellation. This means that a stored symptom constellation that differs more from a specified symptom constellation than another is in particular displayed in a less prominent place or at a later time than a symptom constellation having better congruence.

It is for example preferred to compute the sequence by way of determining the distance squares of each of the symbols to one another. It is in particular possible for different symptoms to show different weightings. It is further particularly preferred for the relevance and/or the expression of a symptom to be included in the weighting. Then a particularly high relevance and/or expression increases the weighting while a low relevance and/or expression decreases the weighting.

The importance or severity of the findings is preferably weighted particularly highly. Serious diseases or findings involving high hazard potential are given higher priority than do harmless diseases or minor technical problems.

Preferably the comparator, following each case of modification of the current symptom constellation, compares the current symptom constellation against the symptom constellations of the findings stored in the data base and adds stored findings to the current list of findings, even if the congruence of the respective symptom constellation with the current symptom constellation remains below the predetermined, first value but lies above a predetermined, third value namely, if the disorder potential of the stored findings exceeds a predetermined threshold. The predetermined third value is preferably less than the predetermined first value and may depend on the severity of the disorder potential of the findings.

The list of findings in particular receives only some of the possible and in particular the most relevant findings. In simple configurations the list of findings may only contain those findings which are displayed on the display device. In other configurations the list of findings may comprise a subset of the entirety of findings included in the data base of which in turn only part is mapped.

It is also possible and preferred to perform a weighting of the stored objects which can be predetermined or dynamically influenced. For example when diagnosing diseases there may be a general weighting according to which more serious diseases are weighted higher than less serious diseases. This allows to give the attending physician a clear indication of serious diseases which the doctor can safely exclude by a corresponding examination to not inadvertently disregard an essential diagnostic option. Serious diseases are preferably placed higher in the list.

The display device is additionally provided with a symptom display in which the list of suggestions is represented by way of a plurality of symptoms. This symptom display is in particular configured as a list of suggestions and aids the user when entering symptoms. The individual symptoms in the list of suggestions may be present classified by symptom type. However, it is particularly preferred for the current list of suggestions to be generated dynamically wherein the first positions list symptoms which provide particularly high differentiation options, i.e. substantial gain in information. For example if used in the medical field there is another symptom by way of the symptom constellation entered thus far which might allow high differentiation then it may make sense in terms of ergonomics to firstly examine this symptom as the next symptom. Thus for example after checking for the presence of this single symptom the list of conceivable diseases may then be considerably reduced while other symptoms would only allow a less distinct differentiation. Therefore it suggests itself to specify the sequence of the symptoms to be entered such that a high relevance can be achieved any time. In this way the efficiency of the selection process is considerably increased.

It is preferred for the comparator to compare the symptoms of the current list of suggestions against the symptoms of the findings of the current list of findings and to classify the current list of suggestions taking into account the seriousness of the findings of the current list of findings. Thus it is possible to place symptoms in front which are significant for findings having high hazard potential or being very severe.

In all the configurations it is preferred for the intensity (expression) of a symptom to determine the size of an inserted symbol. Or else it is also possible for the intensity of a symptom to determine the colour of an inserted symbol or the brightness of an inserted symbol. It is also possible that in dependence on the properties of a symptom the respective symbol is displayed flashing or shown with a pattern.

In all the configurations it is particularly preferred that so-called negative symptoms are specified. A negative symptom is understood to mean a mark defining the absence of the respective symptom. For example the symptom "fever" is a significant symptom in various diseases. High differentiation is attained by way of excluding this symptom. Now if the symptom "fever" is input as a negative symptom this means that the patient does not show fever which may exclude many diseases.

These negative symptoms may be marked as specific symbols or e.g. by a characteristic colour frame or striking out or crossing out the symbol characteristic of the symptom. In particular will they basically be represented like positive symptoms but for example additionally surrounded by a circle.

In all the configurations it is preferred for each symptom of the pertaining symptom constellation to be plotted as a pathology is output, independently of whether or not such a symptom is present in the current symptom constellation so as to facilitate in particular a visual assessment of the current symptom constellation against the symptom constellations of the represented findings of the current list of findings.

The system according to the invention serves to aid in diagnosing an object that shows at least one disorder and for selecting at least one finding that characterises at least part of the state of the object wherein a number of findings is stored in at least one data base. In particular does the system serve to perform a method described previously.

There is provided at least one display device, at least one computer, at least one comparator, at least one memory device, and at least one input device.

At least one pre-defined symptom constellation, at least one pre-defined list of objects with stored findings and at least one pre-defined list of symptoms including conceivable symptoms are stored in the memory device. The computer allows to derive a current list of findings from the pre-defined list of findings, a current list of suggestions from the pre-defined list of suggested symptoms, and a current symptom constellation from the pre-defined symptom constellation.

Each of the findings stored in the memory device is defined as a visual pathology by a severity of the findings and by a symptom constellation of multiple symptoms and by a representation of the symptom constellation that can be graphically output on the display device. Each of the symptoms is defined by at least one symptom type and at least one expression. The expression indicates the subjective significance.

The computer is set up and configured to represent each symptom in each pathology by a symbol. The coordinates of each of the symbols are determined in a first dimension, by the symptom type of the symptom and in a second dimension, by the expression of the symptom. The expression of the symptom is subjectively newly assigned each time, indicating a subjectively perceived significance in respect of the source of the disorder.

The computer is set up and configured to perform a dialog-based, visual modelling of the state of the object. The state of the object is described or approximated by a current symptom constellation. The current symptom constellation may comprise one or more symptoms and more symptoms can be added in the course of the process. Each symptom shows at least one symptom type and at least one expression. The current symptom constellation can be represented as an object image wherein the computer is set up and configured to represent each symptom by a symbol. The coordinates of each of the symbols are determined in a first dimension, by the symptom type of the symptom and in a second dimension, by the expression of the symptom.

The computer is configured and set up to capture the modification of a symptom of the current symptom constellation and to store the current symptom constellation in the memory device.

The computer is configured and set up to automatically and immediately graphically output on the display device the current symptom constellation as the current object image.

The comparator is configured and set up to compare, following each case of symptom modification, the current symptom constellation against the stored symptom constellations of the findings of the current list of findings and to delete from the current list of findings those findings showing a congruence with the current symptom constellation that remains beneath a predetermined, first value.

The comparator is configured and set up to automatically compare, following each entry of a symptom, the current symptom constellation against the symptom constellations of the findings stored in the data base and to add to the current list of objects those stored findings showing a congruence of the respective symptom constellation with the current symptom constellation that lies above a predetermined, second value.

The first and second values may be predetermined or dynamically selected. The first value may be the same as the second value or in particular be lower.

The computer is configured and set up to automatically sort the current list of findings following each case of symptom modification wherein the sorting takes into account the similarity of the current symptom constellation with the respective symptom constellation of the stored findings and the severity of the stored finding.

The computer is configured and set up to plot onto the display device as the pathology, the symptom constellation pertaining to at least one finding of the current list of findings, if the current list of findings includes at least one finding.

The comparator is configured and set up to automatically compare, following each case of symptom modification, the current list of suggested symptoms against the symptoms of the current list of findings, and to re-sort the current list of suggestions.

The computer is configured and set up to immediately output the current list of suggested symptoms.

The computer is in particular configured and set up to store in the memory device the current symptom constellation and in particular also the current list of suggestions and the current list of findings.

The system according to the invention has many advantages since it offers easy and neat aid and assistance with selecting symptom constellations.

In particular is the system according to the invention configured as an in particular mobile and preferably gesture-controlled computer, comprising a touch-sensitive surface by means of which symptoms can be selected and placed. The realisation on a smartphone is also preferred.

BRIEF DESCRIPTION OF THE DRAWINGS

Further advantages and features of the present invention can be taken from the exemplary embodiment which will be described below with reference to the enclosed figures.

The drawings show in.

DETAILED DESCRIPTION

With reference to the enclosed FIGS. 1 to 4 an exemplary embodiment of a method according to the invention with a system 30 according to the invention will be explained below. The system 30 serves to aid in selecting at least one finding or a diagnosis from a group of stored findings and it is in particular provided for use in the medical field although it may be used in analysing technical systems.

The system 30 allows an attending physician and in particular a specialist a simple way of keeping in view even rare diseases by way of comparing the layout of diagnosed symptoms against stored symptom constellations of validated diagnoses.

In this way the user will be able to make a selection between two pathologies or symptom constellations which are relatively appropriate. Misdiagnoses will be largely avoided since the overview of all the symptoms of a clinical picture and the comparison against reliably captured diagnoses makes the decision safer, in particular in medical fields where multiple factors interact. The decision may be made following further examinations as required.

For example since the symptom "vertigo" may be indicative of disorders of the vestibular organ, disorders of the cervical spine or for example also a cerebral infarction while these two disorders show markedly different symptom constellations, the method according to the invention offers by way of graphic comparison of symptom constellations an intuitive, quick, and very efficient aid in interpreting the symptom constellation.

Figure 1:
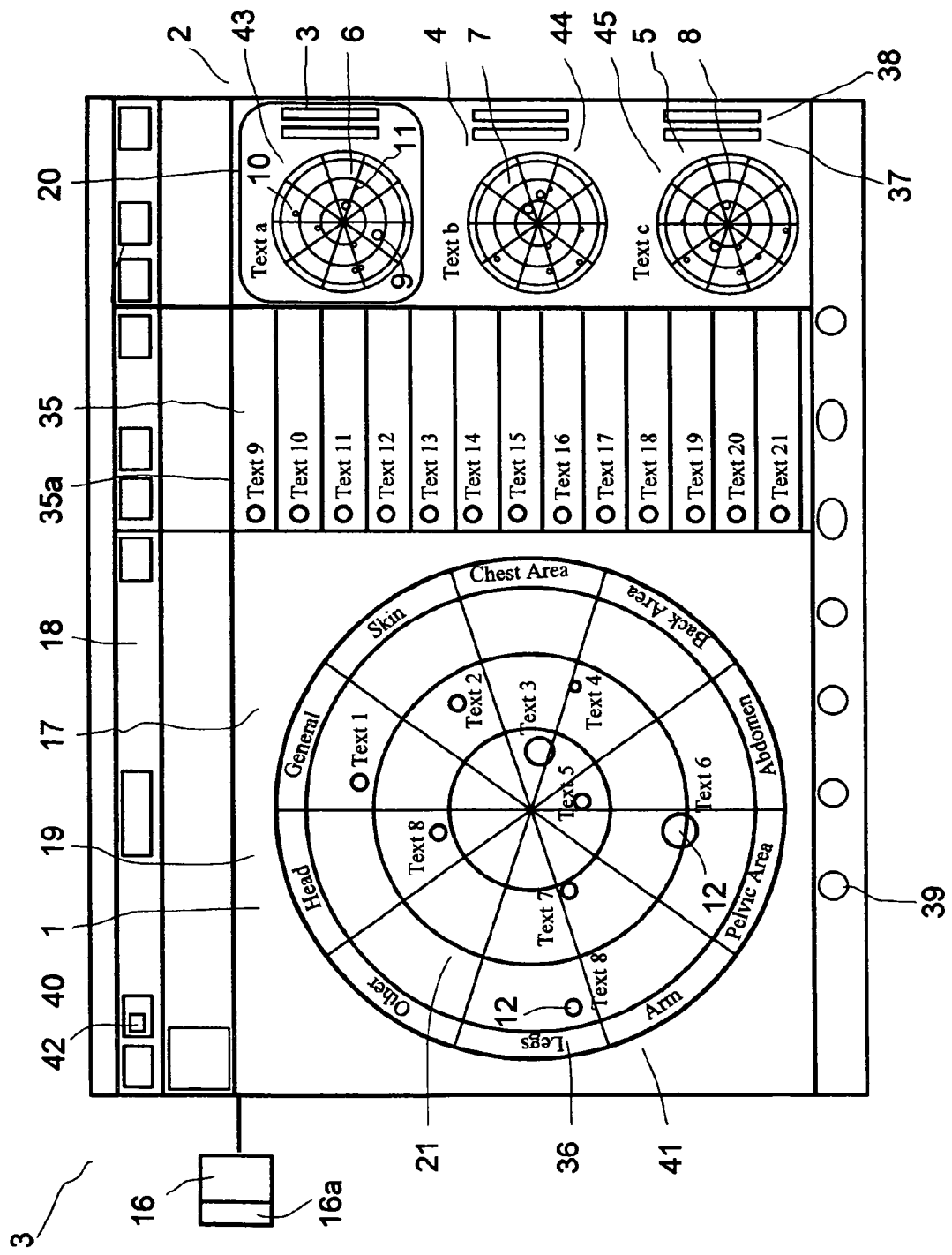
FIG. 1 the surface of a system according to the invention.

FIG. 1 shows a system 30 which is presently for example designed as a hand-held PC and which is equipped with a touch-sensitive surface. Virtually the entire surface of the system 30 is filled by a display device 18 which in the present exemplary embodiment also assumes the function of the input device 17. Optionally it is also possible for a separate input device or multiple separate input devices 17 to be connected. A computer 16 is symbolically drawn in which may comprise a comparator 16a. Or else the comparator 16a may be provided separately. The computer 16 and the comparator 16a may be incorporated via a network connection.

The display is basically divided into three vertical sections with the largest section provided for the view area 19 which presently takes up about half the width.

Thereafter there is a symptom display 35a on the right including a list 35 of suggested symptoms, which in turn is followed by a selection area 20. The list of symptoms 35 lists symptoms which have not yet been positioned on the view area 19.

The system is provided with a data base 42 in which findings 3 to 5 are stored wherein basically any desired plurality of findings can be stored. The data base 42 may be provided locally in a memory device 40 or accessible via a network connection. In the present exemplary embodiment each of the findings 3 to 5 represents a symptom constellation of a disease.

Each of the stored findings 3 to 5 is defined by exactly one symptom constellation 6 to 8. Each of the symptom constellations 6 to 8 includes one or more symptom(s) 9 to 11. Basically the quantity of the symptoms of a symptom constellation is not limited such that more than three, four, five or more symptoms may pertain to one stored finding.

Each of the symptoms is characterised by a symptom type 13 and by a significance or relevance 14, and optionally by an intensity or expression 15. Individual or all of the symptoms may include further properties.

In FIG. 1 a symptom constellation 21 is represented in a graphic representation in the view area 19, the symptom constellation 21 consisting of a plurality of symptoms 22 to 24 which are each drawn into the view area 19 by way of symbols 12. The graphic representation of the current symptom constellation 21 shows the current object image 41 which had been modelled so far while the process was being carried out. When a new symptom is added or else a previously added symptom 22 to 24 is deleted or modified, then the object image 41 is updated automatically and where possible immediately. In this way one attains a high level of interactivity where the user can promptly view the result of his modelling.

In effect, the view area 19 is presently designed as a circular disc with the location of each symbol 12 being defined by an angle and a distance from the centre. The angle is specified by the symptom type 13 and the distance from the centre ensues from the relevance 14 of the respective symptom 22 to 24 for the state of the object 1 or the finding. Each symbol 12 may be provided with an explanatory text "text 1" etc. in the view area 19 which describes or explains the symptom in detail.

The attending physician drags the individual symptoms 22 to 24 etc. into the view area 19 and drops them according to the symptom type 13 and the importance 14. The expression 14 is assigned subjectively by the attending physician.

Assigning a strong expression means that the expert carrying out the method deems the symptom significant to the current state of the object 1 of the object. The same applies in diagnosing patients and also in examining complex technical machinery or installations.

When the operator positions a symbol 12 closer to the centre, this means that in his opinion it has greater significance for the current symptom constellation 21 and thus disease. When the symbol 12 is positioned radially further outwardly then the doctor weights it rather as an accompanying symptom, thus as less significant.

Other than the symptom type 13 and the relevance 14, an intensity 15 can also be assigned to each symptom. In this case for example the intensity of pain is indicated. The patient may for example complain of a headache. The type of pain determines the symptom type 13. The doctor assigns the relevance 14 according to his assessment of the significance of this symptom for the current disease. Finally the doctor can indicate the strength of the pain in a numeric pain scale by the size of the symbol 12.

The computer 16 automatically obtains a list of findings 35 with stored findings 3 to 5 whose symptom constellation 6 to 8 shows a relatively high similarity with the currently input symptom constellation 21. The symptom constellations 6 to 8 of the stored objects 3 to 5 are separately, graphically mapped in the display fields 33 and 34 etc. The display fields 33 and 34 form part of the selection area 20 on the right of the display device 18. In analogy to the symptom constellation 21, each of the symptoms 9 to 11 of the symptom constellation 6 to 8 of the stored objects 3 to 5 are graphically reproduced as a symbol 12. Due to the fact that the type of display of the stored objects 3 to 5 corresponds to the type of display of the symptom constellation 21, there is a high degree of comparability of the object image 41 of the current symptom constellation 21 with the pathologies 43-45 of the stored symptom constellations 6 to 8. For reasons of clarity the explanatory texts of the individual symptoms are as a rule not displayed in the selection area 20.

Thus the doctor can by way of a visual comparison directly determine in which area of the diagram the symbols 12 are positioned in what type and form. Already a frequency distribution of the symbols 12 in different areas 36 allow the doctor to draw helpful conclusions. Since the view area 19 is preferably divided in areas 36 presently in the shape of angular segments which may for example be assigned to different regions of the body, the doctor can quickly identify how the symptoms are distributed over the patient's body.

The distribution of the areas 36 may in particular be dependent on the medical or technical special field in which the system 30 is used. The system 30 is a particular success in aiding the selection of diagnoses made in special fields and in which conventional diagnoses show inadequate results due to their diffuse symptoms.

Due to the visual comparability of the object image 41 of an input symptom constellation 21 against the pathologies 43-45 of the stored symptom constellations 6-8, a simple but still correct selection option is provided.

In the illustration according to FIG. 1 the symptoms positioned in the view area 19 are provided with the explanatory text "text 1" to "text 8". In the list of suggestions 35 the symptoms listed therein are marked with the explanatory text "text 9" to "text 21". The sequence of the symptoms in the list of symptoms or list of suggestions 35 ensues dynamically. The symptom having the highest information content is preferably disposed on top.

Figure 2:
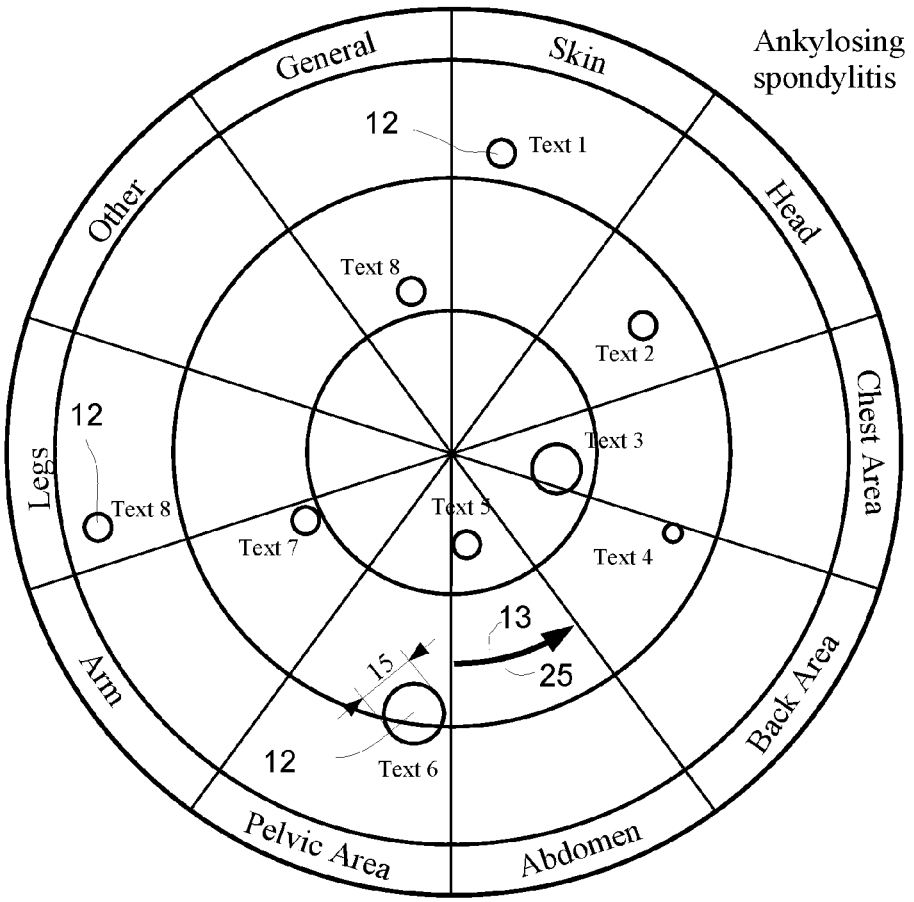
FIG. 2 the view area of the system of FIG. 1.

FIG. 2 shows the enlarged view area 19 of the display device 18 wherein a plurality of symbols 12 is inserted which represent respective symptoms. Each of the symbols 12 represents one symptom type 13, one relevance 14, and a respective intensity 15. The symptom type 13 is plotted in a first dimension 25 as an angular coordinate 31. The significance 14 is plotted in a second dimension 26 in a radial coordinate 32. The intensity 15 is marked by the size or the diameter of a symbol 12.

With reference to the FIGS. 3 and 4 a procedure will now be explained for using the system 30. The doctor drags a symptom 22 to 24 from the list of suggestions 35 as a symbol 12 to the view area 19.

The angular positioning of the symbol 12 on the view area 19 ensues from the symptom type 13 of the symptom. The doctor positions the symbol 12 in a radial spot which in his opinion corresponds to the relevance and thus presently to the significance 13 for the present disease. Presently in this layout significant symptoms are placed radially inwardly and less significant symptoms, radially outwardly. This means that in the case of the present disease the attending physician considers the symptom 22 to be less significant than the symptom 23.

As a consequence of the two entered symptoms 22 and 23 there will be an automatic listing on the right in the selection area 20, of conceivable relevant findings 3 to 5, the sequence of which ensues from the congruence of the respective symptom constellations 6 to 8 with the symptom constellation 21 in the left part of the display device 18 or in the view area 19. Optionally a superposition is selectively possible wherein the object image 41 of an entered symptom constellation 21 and a pathology 43-45 of a stored finding 3-5 are superposed in the view area. Differentiation can be made e.g. by colour.

Between the view areas 19 and the selection area 20 a list of symptoms or current list of suggestions 35 is further provided in which those symptoms are listed which are included in the clinical pictures from the selection list 20 but not in the view area 19. In this respect the symptoms listed therein may also be called differential symptoms. The list is generated dynamically. On top, symptoms are positioned which allow a higher level of differentiation, i.e. provide increased gain in information compared to others. This means that the first symptom positioned on the list 35 is a symptom 22-24 which allows the best possible differentiation between the diagnoses or stored findings 3 to 5 that are presently identified as potentially relevant.

Figure 3:
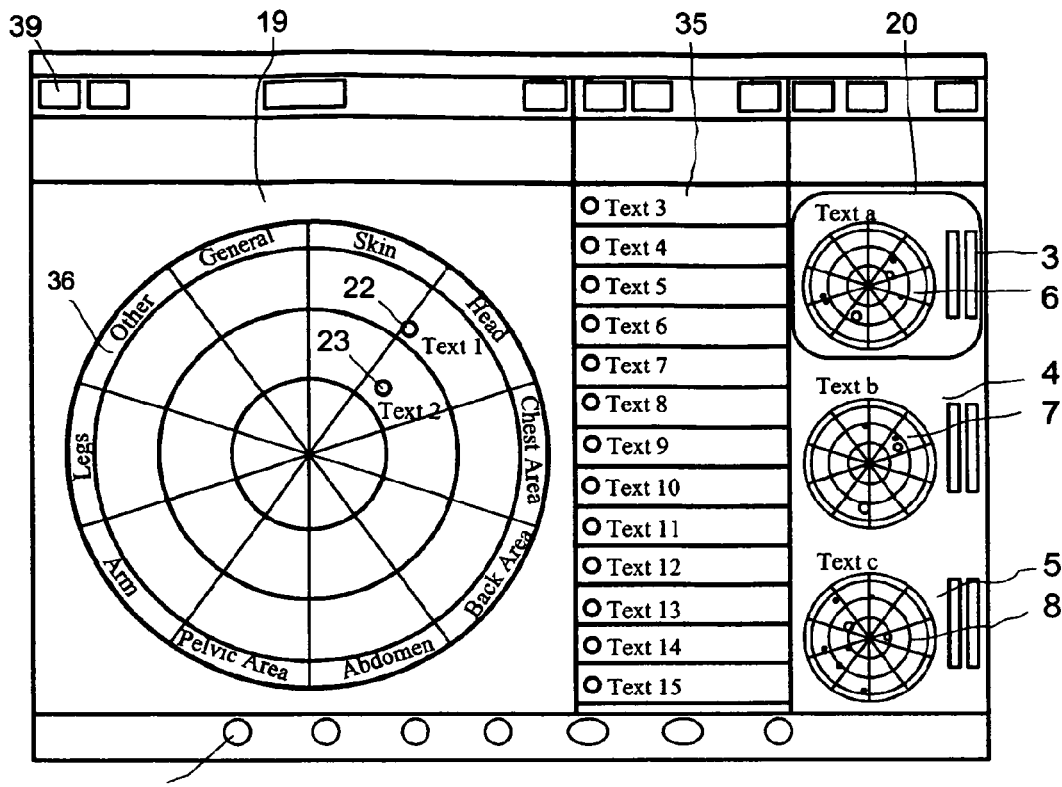
FIG. 3 the display device of the system of FIG. 1 following input of two symptoms.
Figure 4:
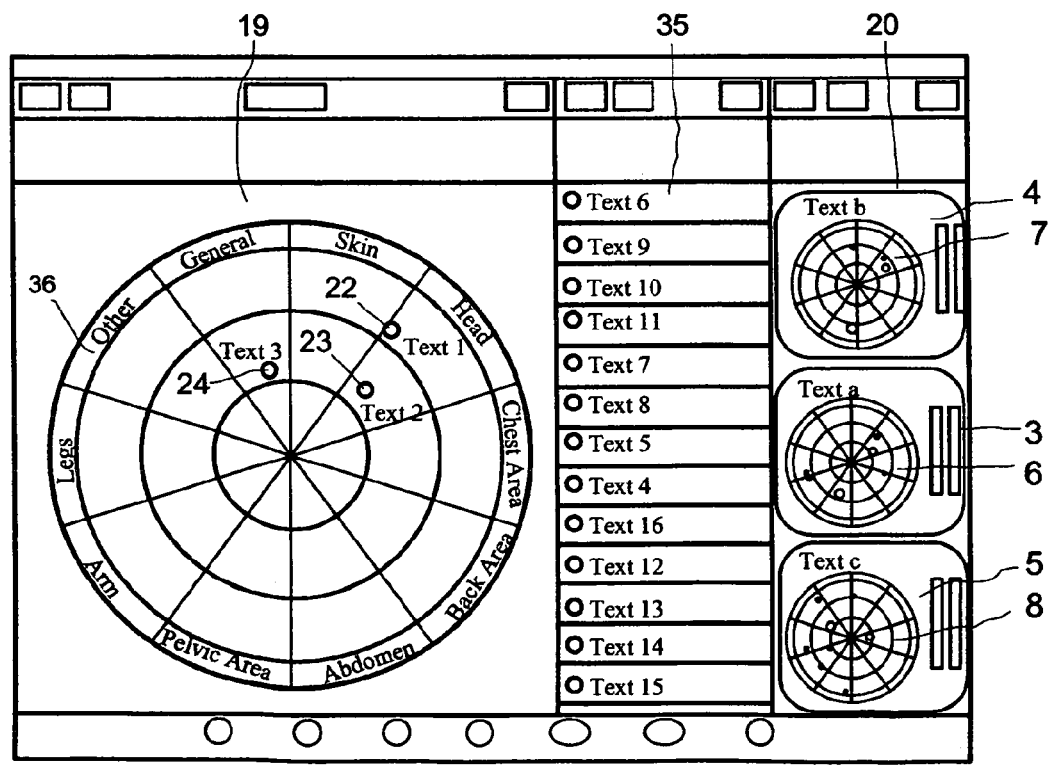
FIG. 4 the display device of the system of FIG. 1 following input of three symptoms.

After placing the symptom 24 including the explanatory text "text 3" in the view area 19, the sequence of the findings 3 and 4 in the selection area 20 changes, as can be seen by comparing the FIGS. 3 and 4. This means that the symptom constellation 7 of finding 4 now shows a higher degree of congruence with the symptom constellation 21 than does the symptom constellation 6 of finding 3.

Furthermore the sequence of the symptoms in the list of suggestions 35 has likewise changed. Thereafter, the symptom including the explanation "text 6" is topmost but not the expected symptom including the explanatory text "text 4" since due to also taking into account the symptom 24 a different weighting ensues on the whole.

Now the doctor may drag one of the symptoms for example from the list of suggestions 35 and drop it in the view areas 19 such that the symptom constellation 21 illustrated in FIG. 4 ensues. Due to the new symptom constellation the sequence of the stored findings 3 to 5 which may be considered as potentially relevant may change accordingly.

Each of the stored findings 3, 4 or its symptom constellation 6, 7, is represented in a separate display field 33, 34 to obtain an unambiguous display each of a symptom constellation.

Figure 5:
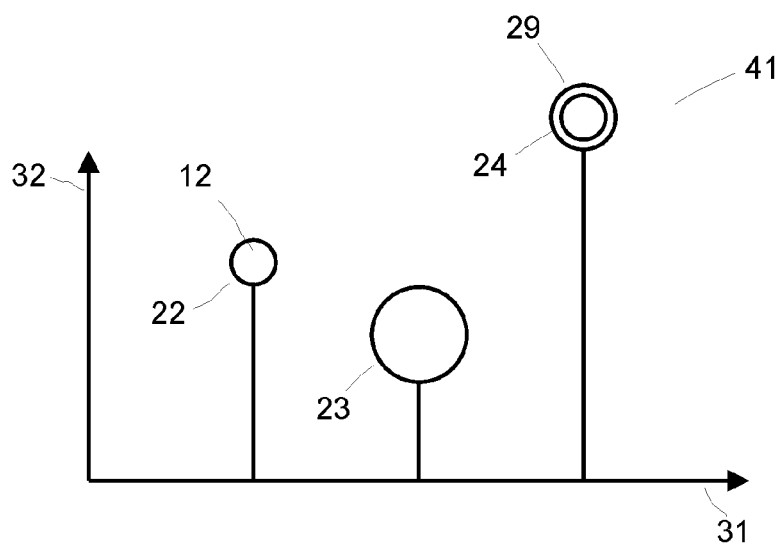
FIG. 5 a schematic illustration of an alternative view area.

FIG. 5 shows a variant of a view area 19 with the display in a usual X-Y diagram on the basis of Cartesian coordinates. The symptom type 13 is plotted over a coordinate 31 and perpendicular thereto the significance 14, over the coordinate 32.

In this kind of layout the shape is not a disk shape but a usual Cartesian coordinate system which also ensues in a characteristic image for each symptom constellation.

In all the cases it is possible to also enter negative symptoms other than symptoms. To this end, negative symptoms 29 are provided which characterise the absence of a symptom. This may be a particularly important symptom since in specific diseases e.g. the presence of fever is characteristic. Now when the doctor finds that the patient does not run a fever then this may considerably limit the selection of conceivable diagnoses. The symptom 24 is presently shown as a negative symptom 29 and has a double circle for a symbol.

On the whole the invention provides a simple system and an advantageous method for visualising a finding by way of a characteristic constellation of symptoms in particular in a defined graphic frame to thus make a quick and intuitive choice. The user will internalise the layout and processing over time and will thus be able to use the system intuitively without involving thought processes.

Closeness to the centre represents the significance 14, the symbol size 15, the intensity, and the circle segment 36 a class of symptom, while the angular degree within the circle segment represents a symptom type 13. Thus there is a system similar to reading a geographical map.

Due to the characteristic positioning of graphic symbols 12 as symptoms 9-11 in an assigned frame a clinical picture can be positioned characteristically and recognisably in a minor spatial size.

The visual-constellative approach allows to also represent semantically complex objects such as so-called statures using minimum space. The observer has a good overview notwithstanding the small size.

LIST OF REFERENCE NUMERALS 1 state of the object
2 list of findings
3-5 stored finding, diagnosis
6-8 symptom constellation
9-11 symptom
12 symbol
13 symptom type
14 expression, relevance, significance
15 intensity, strength
16 computer
16a comparator
17 input device
18 display device
19 view area, diagnosis field
20 selection area, comparison display
21 current symptom constellation, clinical picture
22-24 symptom
25 first dimension, type of symptom
26 second dimension, relevance
27 severity of finding
29 negative symptom
30 system
31, 32 coordinate 33, 34 display field
35 list of suggestions
35a symptom display
36 area
37 display
38 display
39 control component
40 memory device
41 object image
42 data base
43-45 pathology

The invention claimed is:

1. A method for aiding diagnosis of an object showing at least one disorder and for selecting a finding that characterizes at least part of the state of the object, the method comprising:

storing a number of findings in at least one data base;

wherein each of the stored findings is described by a severity of the finding and a symptom constellation of a number of symptoms and by a graphic representation of the symptom constellation, as a visual pathology, wherein each symptom shows at least one symptom type and at least one expression, and wherein each symptom in each pathology is represented by a symbol the coordinates of which are determined in a first dimension by the symptom type of the symptom and in a second dimension by expression of the symptom, wherein the expression is determined by a subjectively perceived significance in respect of the disorder-generating source; and wherein a dialog-based, visual modeling of the state of the object occurs to which end the state of the object is described by a current symptom constellation which may comprise multiple symptoms, wherein each symptom shows at least one symptom type and at least one expression, and wherein the current symptom constellation is represented as an object image wherein each symptom is represented by a symbol whose coordinates are Determined in a first dimension by the symptom type of the symptom and in a second dimension by the expression of the symptom; and wherein to aid diagnosis at least one computer, at least one comparator, at least one input device, and at least one display device are provided;

wherein the following process steps are carried out:

deriving a current symptom constellation from a pre-defined symptom constellation;

deriving a current list of findings from a pre-defined list of findings containing stored findings;

deriving a current list of suggestions for symptoms from a pre-defined list of suggested symptoms;

and wherein the following process steps are automatically repeated in a loop in this or another suitable sequence until a finding is determined manually, or until a pathology and thus the pertaining finding is selected or until the process is abandoned:

a) by way of the input device at least one symptom of the current symptom constellation is modified for modelling the state of the object and the modified symptom constellation is stored as the current symptom constellation and the current symptom constellation is automatically and immediately graphically output on the display device as the current object image;

b) the comparator automatically compares, following each case of symptom modification, the current symptom constellation against the stored symptom constellations of the findings of the current list of findings and immediately deletes from the current list of findings those findings showing a congruence with the current symptom constellation that remains beneath a predetermined, first value;

c) the comparator automatically compares, following each case of symptom modification, the current symptom constellation against the symptom constellations of the findings stored in the data base and immediately adds to the current list of findings those stored findings showing a congruence of the respective symptom constellation with the current symptom constellation that lies above a predetermined, second value;

d) the comparator automatically compares the current symptom constellation against the symptom constellations of the findings stored in the data base and adds stored findings to the current list of findings if the congruence of the respective symptom constellation with the current symptom constellation remains below the predetermined, first value but lies above a predetermined, third value if the disorder potential of the stored finding exceeds a predetermined threshold;

e) the current list of findings is automatically and immediately sorted by the computer following each case of symptom modification, which sorting takes into account the similarity of the current symptom constellation with the respective symptom constellation of the stored findings and the severity of the stored finding;

f) the symptom constellation pertaining to at least one finding of the current list of findings is plotted on the display device as pathology if the current list of findings includes at least one finding; and g) the comparator compares, following each case of symptom modification, the current list of suggestions for symptoms against the symptoms of the findings of the current list of findings, and re-sorts the current list of suggestions, and immediately outputs the current list of suggestions.

2. The method according to claim 1 wherein the display device comprises at least one view area and at least one selection area and wherein the output of the object image occurs in the view area and the output of the at least one pathology, in the selection area.

3. The method according to claim 1 wherein by means of the input device at least one symptom of the state of the object is input, deleted or changed and the current symptom constellation is modified correspondingly.

4. The method according to claim 1 wherein at least one symptom comprises an intensity as a further property.

5. The method according to claim 1 wherein a weighting of different symptoms can be predetermined.

6. The method according to claim 1 wherein the output of the current list of suggestions is provided on a symptom display.

7. The method according to claim 1 wherein a modification of at least one symptom of the current symptom constellation occurs by graphic input.

8. The method according to claim 1 wherein with each input or modification of a symptom the expression is newly defined, indicating a subjective significance of this symptom type for explaining the state of the object.

9. The method according to claim 1 wherein negative symptoms can be specified.

10. The method according to claim 1 wherein upon outputting a pathology each symptom of the pertaining symptom constellation is plotted, independently of whether or not this symptom is present in the current symptom constellation, so as to facilitate in particular a visual assessment of the current symptom constellation against the symptom constellations of the represented findings of the current list of findings.

11. The method according to claim 1 wherein the current list of suggestions is sorted by the distinctiveness of the symptoms contained therein.

12. A method for aiding diagnosis of an object showing at least one disorder and for selecting a finding that characterizes at least part of the state of the object comprising:

storing a number of findings in at least one data base;

wherein each of the stored findings is described by a severity of the finding and a symptom constellation of a number of symptoms and by a graphic representation of the symptom constellation, as a visual pathology; wherein each symptom shows at least one symptom type and at least one expression, and wherein each symptom in each pathology is represented by a symbol the coordinates of which are determined in a first dimension by the symptom type of the symptom and in a second dimension by expression of the symptom, wherein the expression is determined by a subjectively perceived significance in respect of the disorder-generating source; and wherein a dialog-based, visual modeling of the state of the object occurs to which end the state of the object is described by a current symptom constellation which may comprise multiple symptoms, wherein each symptom shows at least one symptom type and at least one expression, and wherein the current symptom constellation is represented as an object image wherein each symptom is represented by a symbol whose coordinates are determined in a first dimension by the symptom type of the symptom and in a second dimension by the expression of the symptom; and wherein to aid diagnosis at least one computer, at least one comparator, at least one input device, and at least one display device are provided;

wherein the following process steps are carried out:

deriving a current symptom constellation from a pre-defined symptom constellation;

deriving a current list of findings from a pre-defined list of findings containing stored findings;

deriving a current list of suggestions for symptoms from a pre-defined list of suggested symptoms;

and wherein the following process steps are automatically repeated in a loop in this or another suitable sequence until a finding is determined manually, or until a pathology and thus the pertaining finding is selected or until the process is abandoned:

a) by way of the input device at least one symptom of the current symptom constellation is modified for modelling the state of the object and the modified symptom constellation is stored as the current symptom constellation and the current symptom constellation is automatically and immediately graphically output on the display device as the current object image;

b) the comparator automatically compares, following each case of symptom modification, the current symptom constellation against the stored symptom constellations of the findings of the current list of findings and immediately deletes from the current list of findings those findings showing a congruence with the current symptom constellation that remains beneath a predetermined, first value;

c) the comparator automatically compares, following each case of symptom modification, the current symptom constellation against the symptom constellations of the findings stored in the data base and immediately adds to the current list of findings those stored findings showing a congruence of the respective symptom constellation with the current symptom constellation that lies above a predetermined, second value;

d) the current list of findings is automatically and immediately sorted by the computer following each case of symptom modification, which sorting takes into account the similarity of the current symptom constellation with the respective symptom constellation of the stored findings and the severity of the stored finding e) the comparator compares the symptoms of the current list of suggestions against the symptoms of the findings of the current list of findings and sorts the current list of suggestions taking into account the seriousness of the findings of the current list of findings;

f) the symptom constellation pertaining to at least one finding of the current list of findings is plotted on the display device as pathology if the current list of findings includes at least one finding; and g) the comparator compares, following each case of symptom modification, the current list of suggestions for symptoms against the symptoms of the findings of the current list of findings, and re-sorts the current list of suggestions, and immediately outputs the current list of suggestions.

13. A method for aiding diagnosis of an object showing at least one disorder and for selecting a finding that characterizes at least part of the state of the object, the method comprising:

storing a number of findings in at least one data base;

wherein each of the stored findings is described by a severity of the finding and a symptom constellation of a number of symptoms and by a graphic representation of the symptom constellation, as a visual pathology; wherein each symptom shows at least one symptom type and at least one expression, the symptom type being drawn in as an angular coordinate and the significance, as at least one of a radial distance and the intensity, as a symbol size, and wherein each symptom in each pathology is represented by a symbol the coordinates of which are determined in a first dimension by the symptom type of the symptom and in a second dimension by expression of the symptom, wherein the expression is determined by a subjectively perceived significance in respect of the disorder-generating source; and wherein a dialog-based, visual modeling of the state of the object occurs to which end the state of the object is described by a current symptom constellation which may comprise multiple symptoms, wherein each symptom shows at least one symptom type and at least one expression, and wherein the current symptom constellation is represented as an object image wherein each symptom is represented by a symbol whose coordinates are determined in a first dimension by the symptom type of the symptom and in a second dimension by the expression of the symptom; and wherein to aid diagnosis at least one computer, at least one comparator, at least one input device, and at least one display device are provided;

wherein the following process steps are carried out:

deriving a current symptom constellation from a pre-defined symptom constellation;

deriving a current list of findings from a pre-defined list of findings containing stored findings;

deriving a current list of suggestions for symptoms from a pre-defined list of suggested symptoms;

and wherein the following process steps are automatically repeated in a loop in this or another suitable sequence until a finding is determined manually, or until a pathology and thus the pertaining finding is selected or until the process is abandoned:
a) by way of the input device at least one symptom of the current symptom constellation is modified for modelling the state of the object and the modified symptom constellation is stored as the current symptom constellation and the current symptom constellation is automatically and immediately graphically output on the display device as the current object image;
b) the comparator automatically compares, following each case of symptom modification, the current symptom constellation against the stored symptom constellations of the findings of the current list of findings and immediately deletes from the current list of findings those findings showing a congruence with the current symptom constellation that remains beneath a predetermined, first value;
c) the comparator automatically compares, following each case of symptom modification, the current symptom constellation against the symptom constellations of the findings stored in the data base and immediately adds to the current list of findings those stored findings showing a congruence of the respective symptom constellation with the current symptom constellation that lies above a predetermined, second value;
d) the current list of findings is automatically and immediately sorted by the computer following each case of symptom modification, which sorting takes into account the similarity of the current symptom constellation with the respective symptom constellation of the stored findings and the severity of the stored finding;
e) the symptom constellation pertaining to at least one finding of the current list of findings is plotted on the display device as pathology if the current list of findings includes at least one finding; and
f) the comparator compares, following each case of symptom modification, the current list of suggestions for symptoms against the symptoms of the findings of the current list of findings, and re-sorts the current list of suggestions, and immediately outputs the current list of suggestions.

14. A method for aiding diagnosis of an object showing at least one disorder and for selecting a finding that characterizes at least part of the state of the object, the method comprising:

storing a number of findings in at least one data base;
wherein each of the stored findings is described by a severity of the finding and a symptom constellation of a number of symptoms and by a graphic representation of the symptom constellation, as a visual pathology; wherein each symptom shows at least one symptom type and at least one expression, and wherein each symptom in each pathology is represented by a symbol the coordinates of which are determined in a first dimension by the symptom type of the symptom and in a second dimension by expression of the symptom, wherein at least one of the color and the size of a symbol define one property of a symptom, and wherein the expression is determined by a subjectively perceived significance in respect of the disorder-generating source; and
wherein a dialog-based, visual modeling of the state of the object occurs to which end the state of the object is described by a current symptom constellation which may comprise multiple symptoms, wherein each symptom shows at least one symptom type and at least one expression, and wherein the current symptom constellation is represented as an object image wherein each symptom is represented by a symbol whose coordinates are determined in a first dimension by the symptom type of the symptom and in a second dimension by the expression of the symptom; and
wherein to aid diagnosis at least one computer, at least one comparator, at least one input device, and at least one display device are provided;
wherein the following process steps are carried out:
deriving a current symptom constellation from a pre-defined symptom constellation;
deriving a current list of findings from a pre-defined list of findings containing stored findings;
deriving a current list of suggestions for symptoms from a pre-defined list of suggested symptoms;
and wherein the following process steps are automatically repeated in a loop in this or another suitable sequence until a finding is determined manually, or until a pathology and thus the pertaining finding is selected or until the process is abandoned:
a) by way of the input device at least one symptom of the current symptom constellation is modified for modelling the state of the object and the modified symptom constellation is stored as the current symptom constellation and the current symptom constellation is automatically and immediately graphically output on the display device as the current object image;
b) the comparator automatically compares, following each case of symptom modification, the current symptom constellation against the stored symptom constellations of the findings of the current list of findings and immediately deletes from the current list of findings those findings showing a congruence with the current symptom constellation that remains beneath a predetermined, first value;
c) the comparator automatically compares, following each case of symptom modification, the current symptom constellation against the symptom constellations of the findings stored in the data base and immediately adds to the current list of findings those stored findings showing a congruence of the respective symptom constellation with the current symptom constellation that lies above a predetermined, second value;
d) the current list of findings is automatically and immediately sorted by the computer following each case of symptom modification, which sorting takes into account the similarity of the current symptom constellation with the respective symptom constellation of the stored findings and the severity of the stored finding;
e) the symptom constellation pertaining to at least one finding of the current list of findings is plotted on the display device as pathology if the current list of findings includes at least one finding; and
f) the comparator compares, following each case of symptom modification, the current list of suggestions for symptoms against the symptoms of the findings of the current list of findings, and re-sorts the current list of suggestions, and immediately outputs the current list of suggestions.

15. A system for aiding diagnosis of an object showing at least one disorder and for selecting at least one finding that characterizes at least part of the state of the object wherein a number of findings is stored in at least one data base, and wherein at least one display device, at least one computer, at least one comparator, at least one memory device, and at least one input device are provided;

wherein at least one pre-defined symptom constellation, at least one pre-defined list of objects with stored findings and at least one pre-defined list of symptoms including conceivable symptoms are stored in the memory device, and wherein the computer allows to derive from the pre-defined list of findings, a current list of findings, and from the pre-defined list of suggested symptoms, a current list of suggestions, and from the pre-defined symptom constellation, a current symptom constellation;

wherein each of the findings stored in the memory device is described by a severity of the findings and by a symptom constellation of a number of symptoms and by a representation of the symptom constellation that may be output graphically on the display device as a visual pathology, and wherein each symptom is defined by at least one symptom type and at least one expression indicating the subjective significance, and wherein the computer is set up and configured to represent each symptom in each pathology by a symbol whose coordinates are determined in a first dimension by the symptom type of the symptom and in a second dimension expression of the symptom, wherein the expression of the symptom indicates a subjectively perceived significance in respect of the disorder-generating source;

wherein the computer is set up and configured to perform a dialog-based, visual modelling of the state of the object wherein the state of the object is described by a current symptom constellation which may comprise multiple symptoms wherein each symptom shows at least one symptom type and at least one expression, and wherein the current symptom constellation can be represented as an object image, wherein the computer is set up and configured to represent each symptom by a symbol whose coordinates are determined in a first dimension by the symptom type of the symptom and in a second dimension by the expression of the symptom;

wherein the computer is configured and set up to capture the modification of a symptom of the current symptom constellation and to store the current symptom constellation in the memory device;

wherein the computer is configured and set up to automatically and immediately graphically output on the display device the current symptom constellation as the current object image;

wherein the comparator is configured and set up to automatically compare, following each case of symptom modification, the current symptom constellation against the symptom constellations of the findings of the current list of findings and to delete from the current list of findings those findings showing a congruence with the current symptom constellation that remains beneath a predetermined, first value;

wherein the comparator is configured and set up to automatically compare, following each entry of a symptom, the current symptom constellation against the symptom constellations of the findings stored in the data base and to add to the current list of objects those stored findings showing a congruence of the respective symptom constellation with the current symptom constellation that lies above a predetermined, second value;

wherein the computer is configured and set up, following each case of symptom modification, to automatically sort the current list of findings wherein the sorting takes into account the similarity of the current symptom constellation with the respective symptom constellation of the stored findings and the severity of the stored finding;

wherein the computer is configured and set up to plot on the display device as a pathology, the symptom constellation pertaining to at least one finding of the current list of findings, if the current list of findings includes at least one finding;

wherein the comparator is configured and set up, following each case of symptom modification, to automatically compare the current list of suggested symptoms against the symptoms of the findings of the current list of findings, and to re-sort the current list of suggestions;

wherein the computer is configured and set up to immediately output the current list of suggested symptoms; and wherein the computer is configured and set up to store in the memory device the current symptom constellation and in particular also the current list of suggestions and the current list of findings.

* * * * *